(12) United States Patent
Favre et al.

(10) Patent No.: US 6,395,262 B1
(45) Date of Patent: *May 28, 2002

(54) COSMETIC COMPOSITION COMPRISING A COPOLYMER AND UTILIZATION OF THE COPOLYMER IN A COSMETIC COMPOSITION

(75) Inventors: Sophie Favre; Nadia Terren, both of Chevilly-Larue; Jacques Michelet, Champlan, all of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/934,660

(22) Filed: Sep. 22, 1997

(30) Foreign Application Priority Data

Sep. 20, 1996 (FR) ............................................. 96 11512

(51) Int. Cl.$^7$ ..................... A61K 7/027; A61K 7/043; A61K 7/030

(52) U.S. Cl. ................... 424/61; 424/63; 424/64; 424/78.03; 424/401; 514/772.4; 514/772.6; 514/772.3; 514/937; 514/938

(58) Field of Search ............... 424/78.03, 78.31, 424/61, 401, 63, 64; 514/772.4, 772.6, 772.3, 937, 938

(56) References Cited

U.S. PATENT DOCUMENTS

| | | | |
|---|---|---|---|
| 5,034,218 A | 7/1991 | Duvel | 424/70 |
| 5,114,706 A | * 5/1992 | Duvel | 424/78.02 |
| 5,288,493 A | 2/1994 | Martino et al. | 424/401 |
| 5,376,146 A | 12/1994 | Casperson et al. | |
| 5,478,555 A | 12/1995 | Bara et al. | 424/78.03 |
| 5,567,426 A | 10/1996 | Nadaud et al. | |
| 5,725,845 A | * 3/1998 | Krog et al. | 424/64 |

FOREIGN PATENT DOCUMENTS

| | | |
|---|---|---|
| EP | 0 416 837 | 3/1991 |
| EP | 0 427 411 | 5/1991 |
| EP | 0 430 473 | 6/1991 |
| JP | 06 256136 | 9/1994 |
| JP | 07 187 950 | 7/1995 |
| JP | 08 081 349 | 3/1996 |
| JP | 08 157323 | 6/1996 |
| WO | WO 94/07563 | 4/1994 |
| WO | WO 95/03778 | 2/1995 |
| WO | WO 95/12381 | 5/1995 |

OTHER PUBLICATIONS

English language Derwent Abstract of WO 95/12381; 05/95; PCT.
Patent Abstracts of Japan Pub. No. 07–187950; Jul. 25, 1995, "Oil–In–Water Type Cosmetic", Onaki Minoru.
Patent Abstracts of Japan Pub. No. 06–256136; Sep. 13, 1994, "Transparent Or Translucent Cosmetic", Tamura Hiroaki.
Patent Abstracts of Japan Pub. No. 08–157323; Jun. 18, 1996, "Oily Cosmetic", Hokao Emi et al.
Patent Abstracts of Japan Pub. No. 08–081349; Mar. 26, 1996, "Cosmetic", Ogawa Asuka.
Principles of Polymer Science & Technology In Cosmetics and Personal Care E.D. Goddard Editor pps. 607, 641, 642 J.V. Gruber, 1999.*

* cited by examiner

Primary Examiner—Thurman K. Page
Assistant Examiner—Humera N. Sheikh
(74) Attorney, Agent, or Firm—Finnegan, Henderson, Farabow, Garrett & Dunner, L.L.P.

(57) ABSTRACT

A composition, in particular a cosmetic composition, which may be in the form of an emulsion, the said composition comprising a specific copolymer comprised of monoolefinically unsaturated $C_3$–$C_6$ carboxylic acid monomer and fatty-chain monomeric ester of acrylic acid. The invention also relates to the use of the said copolymer in cosmetics, in particular for improving the staying power of the composition.

20 Claims, No Drawings

COSMETIC COMPOSITION COMPRISING A COPOLYMER AND UTILIZATION OF THE COPOLYMER IN A COSMETIC COMPOSITION

The present invention relates to a composition, especially a cosmetic composition, which may in particular be in the form of an emulsion and may be used to care for and/or make up the human skin, semi-mucous membranes, lips, mucous membranes, inner part of the eyelid and/or the exoskeleton.

Cosmetic compositions, in particular make-up compositions such as lipsticks and foundations, generally comprise fatty substances such as oils and waxes, and a particulate phase generally composed of fillers and pigments. They may thus be, for example in the case of lipsticks, in the form of a stick or tube or in the form of a soft paste. Make-up compositions may also comprise water or a hydrophilic phase and may then be in particular in the form of an oil-in-water emulsion, a water-in-oil emulsion, a multiple emulsion, an aqueous gel or solution, in particular when it is a foundation, a tinted cream, a care cream or an antisun product.

When they are applied to the skin, mucous membranes or semi-mucous membranes, these compositions have the drawback of transferring. This means that the composition is liable to become at least partly deposited on certain supports with which it is placed in contact, such as, for example, a glass, clothing or the skin.

On becoming deposited, the said composition leaves a trace on the support. This thus results in mediocre persistence of the composition on the skin or the mucous membranes, making it necessary to make repeat applications regularly.

Moreover, the appearance of unacceptable traces on certain items of clothing and in particular on blouse collars may discourage certain women from using this type of make-up.

Another drawback of these compositions lies in the problem of migration, since it has been observed that certain compositions have a tendency to migrate into fine lines and/or wrinkles on the skin in the case of foundations; into the fine lines around the lips in the case of lipsticks; and into the folds of the eyelids in the case of eye-shadows. The appearance of lines in the make-up, generated by the movements of the eyelids, has also been observed, especially in the case of eye-shadows.

All these phenomena give rise, on one hand, to a loss of staying power of the composition (that is to say that the composition, by transferring, or by migrating, loses some of its components and/or loses some of its homogeneity), and on another hand, to an unaesthetic effect which it would clearly be desirable to avoid.

Many cosmeticians have been interested in "transfer-free" cosmetic compositions for several years, in particular transfer-free lipsticks and foundations. Thus, transfer-free lipstick compositions containing from 1 to 70% by weight of liquid silicone resin containing repeating silicate units containing alkyl or phenyl pendant chains, from 10 to 98% by weight of a cyclic volatile silicone oil and pulverulent fillers have been envisaged.

Transfer-free lipsticks containing a volatile silicone and a silicone resin containing a pendant esterified chain having at least 12 carbon atoms have also been envisaged.

In general, it is now known that, although the combination of volatile oils with certain silicone compounds makes it possible to obtain a satisfactory transfer-free result, it nevertheless has the drawback of leading, after evaporation of the volatiles, to a film which is not of optimum comfort, in particular since it is not possible to add oils other than silicone oils to these compositions while at the same time retaining a correct transfer-free quality. The reason for this is that hydrocarbon oils, which are known to provide, in particular, a sensation of comfort to a cosmetic composition, have the drawback of increasing the transfer of such a composition.

The need thus remains for a composition, especially a cosmetic composition, which limits, decreases, and or eliminates transfer altogether, and especially a composition which undergoes little or no transfer (that is to say a transfer-free composition), which at the same time has good cosmetic properties, in particular properties of slipperiness and of a sensation of freshness when applied, as well as qualities of softness and comfort after the make-up is applied.

Now, the inventors have demonstrated, surprisingly and unexpectedly, that the presence of a specific copolymer, defined below, in a cosmetic composition makes it possible to limit, or even eliminate entirely, the transfer and/or migration of the said composition and thus makes it possible to improve its staying power. The aim of the present invention is thus to propose a composition which makes it possible to obtain a film of very good staying power, which does not transfer and which does not stain a support with which it might come into contact.

The subject of the invention is thus the use in a cosmetic, dermatological, hygiene and/or pharmaceutical composition of at least one optionally crosslinked copolymer comprising a major fraction derived from at least one first monomer selected from a monoolefinically unsaturated $C_3$–$C_6$ carboxylic acid monomer and an anhydride thereof and a minor fraction derived from at least one second monomer selected from a fatty-chain monomeric ester of an acrylic acid, for the purpose of limiting, decreasing and/or removing altogether the transfer and/or migration of the said composition.

The subject of the invention is also the use of such a copolymer in a cosmetic, dermatological, hygiene and/or pharmaceutical composition in order to improve the staying power of the said composition.

The subject of the invention is also the use of such a copolymer in a cosmetic, dermatological, hygiene and/or pharmaceutical composition, as an agent for limiting, decreasing and/or removing altogether the transfer and/or migration of the said composition, and/or as an agent for improving the staying power of the said composition.

Another subject of the invention is the use of at least one optionally crosslinked copolymer comprising a major fraction derived from at least one first monomer selected from a monoolefinically unsaturated $C_3$–$C_6$ carboxylic acid monomer and an anhydride thereof and a minor fraction derived from at least one second monomer selected from a fatty-chain monomeric ester of an acrylic acid in a cosmetic, dermatological, hygiene and/or pharmaceutical composition, in order to form a film of said composition, said film not transferring and/or not migrating and/or having an improved staying power.

Another subject of the invention is the use of at least one optionally crosslinked copolymer comprising a major fraction derived from at least one first monomer selected from a monoolefinically unsaturated $C_3$–$C_6$ carboxylic acid monomer and an anhydride thereof and a minor fraction derived from at least one second monomer selected from a fatty-chain monomeric ester of an acrylic acid in a transfer-free composition.

By transfer-free composition, one means a composition which transfers very little or which does not transfer at all, according to the meaning developed hereinabove.

Another subject of the invention is a cosmetic, dermatological, hygiene and/or pharmaceutical composition in the form of, and/or comprising, an oil-in-water emulsion, a water-in-oil emulsion, a multiple emulsion or a multi-phase solution, also comprising at least one optionally crosslinked copolymer comprising a major fraction derived from at least one first monomer selected from a monoolefinically unsaturated $C_3$–$C_6$ carboxylic acid monomer and an anhydride thereof and a minor fraction derived from at least one second monomer selected from a fatty-chain monomeric ester of an acrylic acid and at least one pigment having a hydrophobic surface.

Another subject of the invention is a cosmetic, dermatological, hygiene and/or pharmaceutical composition in the form of, and/or comprising, an aqueous gel, an aqueous, aqueous-alcoholic or multi-phase solution, also comprising at least one such copolymer and at least one water-soluble dye.

Another subject of the invention is a transfer-free make-up or care composition comprising at least one optionally crosslinked copolymer comprising a major fraction derived from at least one first monomer selected from a monoolefinically unsaturated $C_3$–$C_6$ carboxylic acid monomer and an anhydride thereof and a minor fraction derived from at least one second monomer selected from a fatty-chain monomeric ester of an acrylic acid.

Another subject of the invention is a transfer-free foundation comprising at least one optionally crosslinked copolymer comprising a major fraction derived from at least one first monomer selected from a monoolefinically unsaturated $C_3$–C6 carboxylic acid monomer and an anhydride thereof and a minor fraction derived from at least one second monomer selected from a fatty-chain monomeric ester of an acrylic acid.

Another subject of the invention is a process for limiting, decreasing and/or preventing the transfer of a cosmetic, dermatological, hygiene and/or pharmaceutical composition, in particular a composition to make up or care for the skin, mucous membranes, semi-mucous membranes and/or the exoskeleton, which comprises the step of including, for one of said purposes, in the said composition an amount effective of at least one such copolymer.

A last subject of the invention is a process for making up the skin, the semi-mucous membranes, the mucous membranes and/or the exoskeleton, comprising the step of applying on said skin, semi-mucous membranes, mucous membranes and/or exoskeleton, a composition or a foundation such as those defined hereinabove.

WO 95/03778, the disclosure of which is specifically incorporated by reference herein, discloses a composition for forming a peelable mask comprising a copolymer such as the one defined hereinabove. Nevertheless, in WO 95/03778, this copolymer is used in order to improve the adhesion of the mask to the skin and not in order to limit, decrease and/or remove the transfer and/or the migration of said composition or in order to improve its staying power.

It has been observed that the compositions comprising the said polymer make it possible to obtain a film having good affinity for the skin and mucous membranes, which may be reflected in better staying power of the film over time and good persistence of its homogeneity.

The compositions according to the invention are easy to apply to the skin and make it possible, inter alia, to obtain make-up products having a relatively non-sticky texture, which remain comfortable to wear throughout the day.

Furthermore, their cosmetic properties are very advantageous: they provide a sensation of freshness when applied, as well as great softness afterwards, and a unifying and comfortable make-up.

Lastly, the compositions according to the invention may be removed easily, in particular with conventional cleansing agents.

The compositions according to the invention especially find a particularly advantageous application in the field of caring for and/or making up the skin, mucous membranes, semi-mucous membranes and the exoskeleton. The expression mucous membranes is understood in particular to refer to the inner part of the lower eyelid; semi-mucous membranes is understood to refer more particularly to the lips of the face; exoskeleton is understood to refer to the eyelashes, eyebrows, hair and nails. Thus, the invention finds a quite specific application in the field of products to care for and/or make up the lips of the face and the skin, such as foundations, lipsticks, self-tanning agents or antisun products.

The compositions according to the invention thus comprise at least one crosslinked copolymer comprising a major fraction derived from at least one first monomer selected from a monoolefinically unsaturated $C_3$–$C_6$ carboxylic acid monomer and an anhydride thereof and a minor fraction derived from at least one second monomer selected from a fatty-chain monomeric ester of an acrylic acid. This copolymer may optionally be crosslinked.

The copolymer according to the invention may be prepared by polymerizing a predominant amount of monoolefinically unsaturated carboxylic monomer or its anhydride, with a smaller amount of fatty-chain acrylic ester monomer. The amount of carboxylic monomer or its anhydride ranges preferably from 80 to 98% by weight and more particularly from 90 to 98% by weight; the acrylic ester is preferably present in amounts ranging from 2 to 20% by weight and more particularly from 2 to 10% by weight; the percentages are calculated relative to the weight of the two monomers.

The preferred carboxylic monomers are chosen from those corresponding to the formula: $CH_2$=CR—COOH in which R denotes hydrogen, halogen, hydroxyl, a lactone group, a lactam group, a cyanogen (—CN) group, a monovalent alkyl group, an aryl group, an alkylaryl group, an aralkyl group or a cycloaliphatic group.

The carboxylic monomers which are particularly preferred are chosen from acrylic acid, methacrylic acid and maleic anhydride, and mixtures thereof.

The fatty-chain acrylic monomeric esters are preferably chosen from those corresponding to the formula: $CH_2$=$CR^1$—$COOR^2$ in which $R^1$ is chosen from hydrogen, methyl and ethyl and $R^2$ is chosen from a $C_8$–$C_{30}$ alkyl group, a $C_8$–$C_{30}$ oxyalkylene group and a $C_8$–$C_{30}$ carbonyloxyalkylene group.

The ester monomers which are particularly preferred are those for which $R^1$ is hydrogen or methyl, and/or those for which $R^2$ is a $C_{10}$–$C_{22}$ alkyl group. Mention may be made in particular of decyl, lauryl, stearyl, behenyl or melissyl acrylates and methacrylates.

Some of the copolymers according to the invention are described in particular in application EP-A-0,268,164, the disclosure of which is specifically incorporated by reference herein, and are obtained according to the preparation methods described in that same document.

Mention may be made more particularly of the copolymers sold under the name Pemulen by the company Goodrich, and in particular the acrylate/$C_{10}$–$C_{30}$-alkylacrylate copolymer such as the product Pemulen TR2.

A mixture of several copolymers as defined above may be used.

These copolymers may generally be present in the compositions according to the invention at a concentration of from 0.01 to 3% by weight relative to the total weight of the composition, preferably 0.02 to 0.6% by weight and more preferably 0.05 to 0.2% by weight.

The composition according to the invention may also comprise a crosslinked and at least 90% neutralized poly(2-acrylamido-2-methylpropane sulphonic acid) polymer since it has been observed that the presence of such a polymer makes it possible to obtain more cosmetically pleasant properties, such as softness and ease of spreading, with a wide viscosity range for the final compositions, which may extend from the form of a liquid milk to the form of a cream.

This crosslinked and virtually or totally neutralized poly(2-acrylamido-2-methylpropanesulphonic acid) polymer is generally water-soluble or water-swellable. It may be characterized in that it comprises, distributed randomly:

a) from 90 to 99.9% by weight of units of general formula (1) below:

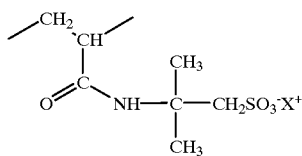

(1)

in which $X^+$ denotes a cation or a mixture of cations, not more than 10 mol % of the cations $X^+$ being able to be protons $H^+$; and b) from 0.01 to 10% by weight of crosslinking units derived from at least one monomer having at least two olefinic double bonds; the proportions by weight being defined relative to the total weight of the polymer.

This polymer preferably comprises from 98 to 99.5% by weight of units of formula (1) and from 0.2 to 2% by weight of crosslinking units.

The cation $X^+$ represents a cation or a mixture of cations chosen in particular from a proton, an alkali metal cation, a cation equivalent to that of an alkaline-earth metal or the ammonium ion. The preferred cation $X^+$ is the $NH_4^+$ cation. More particularly, 90 to 100 mol % of the cations are $NH_4^+$ cations and 0 to 10 mol % are protons ($H^+$).

The crosslinking monomers having at least two olefinic double bonds are chosen, for example, from dipropylene glycol diallyl ether, polyglycol diallyl ethers, triethylene glycol divinyl ether, hydroquinone diallyl ether, tetrallyl oxethanoyl or other allyl or vinyl polyfunctional alcohol ethers, tetraethylene glycol diacrylate, triallylamine, trimethylolpropane diallyl ether, methylenebisacrylamide or divinylbenzine.

The crosslinking monomers having at least two olefinic double bonds are chosen more particularly from those corresponding to the general formula (2) below:

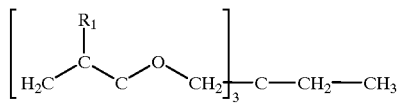

(2)

in which $R_1$ denotes a hydrogen atom or a $C_1$–$C_4$ alkyl radical and more particularly the methyl radical (trimethylolpropane triacrylate).

The polymers particularly preferred are those having a viscosity, measured with a Brookfield viscometer, rotor 4, at a spin speed of 100 revolutions/minute, at 25° C. and as a 2% by weight aqueous solution, of greater than or equal to 1000 cps (1000 mPa.s) and more preferably ranging from 5000 cps to 40,000 cps (5000 to 40,000 mPa.s) and more particularly from 6500 cps to 35,000 cps.

The crosslinked, virtually or totally neutralized poly(2-acrylamido-2-methylpropanesulphonic acids) may be preferably present in the compositions according to the invention at a concentration of from 0 to 20% by weight relative to the total weight of the composition, more preferably 0.1 to 5% by weight and most preferably 0.4 to 2% by weight.

The compositions of the invention also contain a cosmetically, hygienically, pharmaceutically or dermatologically acceptable medium, that is to say a medium which is compatible with any keratin substance, such as the skin, the nails, the hair, the eyelashes and the eyebrows, mucous membranes and semi-mucous membranes and any other area of body or facial skin.

The said compositions contain a cosmetically and/or dermatologically acceptable aqueous medium. In a preferred embodiment, the composition according to the invention is in the form of an oil-in-water emulsion. However, it may also be in the form of a water-in-oil emulsion, a multiple emulsion, an aqueous gel or an aqueous, aqueous-alcoholic or multi-phase solution, in particular water/powder and water/oil/powders.

The aqueous phase of the composition according to the invention may comprise water, a flower water such as cornflower water and/or a mineral water such as eau de Vittel, eau de Lucas or eau de La Roche Posay and/or a spring water. The said aqueous phase may be present at a content of from 15 to 99.9% by weight relative to the total weight of the composition, preferably 40 to 90% by weight, when the composition is in the form of an oil-in-water emulsion, or preferably 85 to 95% by weight when the composition is in the form of a gel or an aqueous solution.

In addition, the aqueous phase may comprise from 0% to 14% by weight, relative to the total weight of the aqueous phase, of a $C_2$–$C_6$ lower monoalcohol and/or of a polyol such as glycerol, butylene glycol, isoprene glycol, propylene glycol or polyethylene glycol.

The composition according to the invention may comprise a fatty phase comprising, in particular, fatty substances that are liquid at 25° C., such as oils of animal, plant, mineral or synthetic origin.

When the composition according to the invention is in the form of an emulsion, the said fatty phase may comprise any cosmetically acceptable oil provided that the said oil makes it possible, by mixing with the aqueous phase and the optional additives, to obtain a stable emulsion, that is to say an emulsion which does not break and which remains in the form of a single phase for at least 24 hours after storage at 25° C., without any phenomenon of creaming or of release of oil.

The oils which may be used may optionally be volatile at room temperature (20–25° C.). The term volatile oil refers to any compound liable to evaporate on contact with the skin. Preferably, oils whose flashpoint is sufficiently high to allow these oils to be used in formulation, and sufficiently low to obtain the desired evanescent effect, are used. Oils whose flashpoint ranges from about 40–100° C. are preferably used. These volatile compounds may be chosen in particular from cyclic or linear silicone oils and/or hydrocarbon oils, alone or as a mixture. Mention may thus be made of volatile silicone oils such as:

cyclic volatile silicones having from 3 to 8, and preferably from 4 to 6, silicon atoms. These are, for example, cyclotetradimethylsiloxane, cyclopentadimethylsiloxane or cyclohexadimethylsiloxane, cyclocopolymers of the dimethylsiloxane/methylalkylsiloxane type, such as Silicone FZ 3109 sold by the company Union Carbide, which is a dimethylsiloxane/methyloctylsiloxane cyclocopolymer, linear volatile silicones having from 2 to 9 silicon atoms. These are, for example, hexamethyl-disiloxane or a PDMS of low viscosity (1 cSt). Mention may also be made of alkyltrisiloxanes such as hexylheptamethyltrisiloxane or octylheptamethyl-trisiloxane.

Mention may also be made of volatile hydrocarbon oils, such as isoparaffins and in particular isododecane.

Among the non-volatile oils, mention may be made of:

poly($C_1$–$C_{20}$)alkyl siloxanes and in particular those containing trimethylsilyl end groups, preferably those whose viscosity is less than 0.06 $m^2$/s, among which mention may be made of linear polydimethylsiloxanes and alkylmethylpolysiloxanes such as cetyldimethicone (CTFA name), silicones modified with optionally fluoro aliphatic and/or aromatic groups or with functional groups such as hydroxyl, thiol and/or amine groups, phenylated silicone oils, in particular those of formula:

(I)

$$\left[\begin{array}{c} \text{R} \\ \text{CH}_3-\text{Si}-\text{O} \\ \text{R} \end{array}\begin{array}{c} \text{Ph} \\ \text{Si}-\text{O} \\ \text{Ph} \end{array}\right]_n \left[\begin{array}{c} \text{Ph} \\ \text{Si}-\text{O} \\ \text{O}-\text{Si}(\text{CH}_3)_3 \\ \text{CH}_3 \end{array}\begin{array}{c} \text{R} \\ \text{Si}-\text{CH}_3 \\ \text{R} \end{array}\right]_m$$

in which R is independently a $C_1$–$C_{30}$ alkyl radical, an aryl radical or an aralkyl radical, n is an integer ranging from 0 to 100, and m is an integer ranging from 0 to 100, with the proviso that the sum of n and m ranges from 1 to 100;

oils of animal, plant or mineral origin, such as liquid paraffin, liquid petroleum jelly, perhydro-squalene, apricot oil, wheatgerm oil, sweet almond oil, beauty-leaf oil, sesame oil, macadamia oil, grapeseed oil, rape seed oil, coconut oil, groundnut oil, palm oil, castor oil, avocado oil, jojoba oil, olive oil or cereal germ oil; fatty acid esters of polyol, in particular liquid triglycerides; alcohols; acetylglycerides; octanoates, decanoates or ricinoleates of alcohols or of polyalcohols; fatty acid triglycerides; glycerides, fluoro oils and perfluoro oils; mixtures thereof.

In one particular embodiment of the invention, an emulsion may be prepared which comprises only silicone fatty substances, such as volatile cyclic oils optionally mixed with PDMSs and/or phenyl silicone oils, or silicone gums, in particular phenylated and/or hydroxylated silicone gums, mixed with optionally volatile silicone oils.

Preferably, the composition comprises a maximum of about 10% by weight of non-volatile hydrocarbon oil; in particular, the composition may comprise less than 8% by weight of non-volatile hydrocarbon oil, more preferably less than 5% by weight, or even no non-volatile hydrocarbon oil at all.

When the composition is in the form of an oil-in-water emulsion, the fatty phase of the emulsion may be generally present at a content of from 2% to 40% by weight relative to the total weight of the emulsion, preferably from 3% to 30% by weight and in particular from 3% to 20% by weight.

The composition according to the invention may also comprise other fatty substances, which may be chosen by a person skilled in the art on the basis of his or her general knowledge, so as to impart the desired properties to the final composition, for example consistency, texture and/or transfer. These additional fatty substances may be waxes, gums and/or pasty fatty substances of animal, plant, mineral or synthetic origin, as well as mixtures thereof.

Mention may be made in particular of:

silicone gums, waxes of animal, plant, mineral or synthetic origin such as microcrystalline waxes, paraffin, petrolatum, petroleum jelly, ozokerite and montan wax; beeswax, lanolin and derivatives thereof; candelilla wax, ouricurry wax, carnauba wax, Japan wax, cocoa butter, cork fibre wax or sugar-cane wax; hydrogenated oils that are solid at 25° C., ozokerites, fatty esters and glycerides that are solid at 25° C.; polyethylene waxes and the waxes obtained by Fischer-Tropsch synthesis; hydrogenated oils that are solid at 25° C.; lanolins; fatty esters that are solid at 25° C.; silicone waxes; fluoro waxes; mixtures thereof.

The composition according to the invention may also comprise one or more cosmetically acceptable (acceptable tolerance, toxicology and feel) organic solvents. These organic solvents may represent from 0% to 98% of the total weight of the composition. They may be chosen from the group comprsing hydrophilic organic solvents, lipophilic organic solvents, amphiphilic solvents and mixtures thereof.

Among the hydrophilic organic solvents, mention may be made, for example, of linear or branched lower monoalcohols having from 1 to 8 carbon atoms, such as ethanol, propanol, butanol, isopropanol or isobutanol; polyethylene glycols having from 6 to 80 ethylene oxides; polyols such as propylene glycol, isoprene glycol, butylene glycol, glycerol or sorbitol; mono- or dialkyl isosorbides in which the alkyl groups have from 1 to 5 carbon atoms; glycol ethers such as diethylene glycol monomethyl or monoethyl ether and propylene glycol ethers such as dipropylene glycol methyl ether. As amphiphilic organic solvents, mention may be made of polybis such as polypropylene glycol (PPG) derivatives, such as fatty acid esters of polypropylene glycol and fatty alcohol ethers of PPG, for instance PPG-23 oleyl ether and PPG-36 oleate. As lipophilic organic solvents, mention may be made, for example, of fatty esters such as diisopropyl adipate, dioctyl adipate and alkyl benzoates.

When the composition according to the invention is in the form of an emulsion, it may optionally also comprise a surfactant, although this is not necessary in order to obtain a stable and fine emulsion. However, the surfactant makes it possible to refine the emulsion obtained. As O/W surfactant, mention may be made in particular of (CTFA): cetearylglucoside, PEG-40 stearate, sorbitan tristearate, sorbitan stearate, polysorbate 60, the mixture sorbitan stearate/sucrose cocoate, the mixture of glyceryl stearate/PEG-100 stearate, PEG400, glyceryl stearate, the mixture of PEG-6/PEG-32/glycol stearate. As W/O surfactant, mention may be made in particular of the mixture polyglyceryl-4 isostearate/cetyldimethicone copolyol/hexyl laurate and the mixture mineral oil/petrolatum/ozokerite/glyceryl oleate/lanolin alcohol.

It may also comprise 0 to 5% by weight, relative to the total weight of the emulsion, of at least one co-emulsifier which may be chosen from oxyethylenated sorbitan monostearate, fatty alcohols such as stearyl alcohol or cetyl alcohol, and fatty acid esters of polyols such as glyceryl stearate or polyglyceryl 10-decaoleate.

In addition, the emulsion according to the invention may comprise one or more thickeners in preferential concentrations of from 0 to 6% by weight, relative to the total weight of the emulsion. The thickener may be chosen from:

polysaccharide biopolymers such as xanthan gum, carob gum, guar gum, alginates and modified celluloses such as hydroxyethylcellulose, methylcellulose, hydroxypropylcellulose and carboxymethylcellulose, synthetic polymers such as polyacrylic acids such as polyglyceryl (meth)acrylate polymers, such as Hispagel or Lubragel from the companies Hispano Quimica or Guardian, polyvinylpyrrolidone, polyvinyl alcohol, crosslinked polymers of acrylamide and of ammonium acrylate such as PAS 5161 or Bozepol C from Hoechst; acrylate/octylacrylamide copolymers such as Dermacryl from National Starch; polyacrylamide-based polymers such as Sepigel 305 from Seppic, crosslinked polymers of acrylamide and of methacryloyloxyethyltrimethylammonium chloride such as Salcare SC 92 from Allied Colloids, magnesium aluminium silicate, inorganic thickeners such as smectites, and modified or unmodified hectorites (Bentone or Laponite, for example), mixtures thereof.

In a preferred manner, the crosslinked and at least 90% neutralized poly(2-acrylamido-2-methylpropanesulphonic acid) polymer as defined above is used as gelling agent.

In another preferred embodiment, an optionally crosslinked acrylic acid homo- or copolymer, or one of the salts thereof, such as those marketed under the name "Carbopol" by the company Goodrich is used as thickening polymer. Such a thickening polymer effectively makes it possible, in particular, to obtain a physically and cosmetically pleasant product, especially one which is smooth and of satisfactory application, with a viscosity which may range from fluid milk to cream.

The composition according to the invention may also comprise a particulate phase which may comprise pigments and/or pearlescent agents and/or fillers commonly used in cosmetic compositions. The term pigments should be understood to refer to white or coloured, inorganic or organic particles which are insoluble in the medium, these being intended to colour and/or opacify the composition. Fillers should be understood as referring to colourless or white, inorganic or synthetic, lamellar or non-lamellar particles intended to give body or rigidity to the composition, and/or softness, a matte effect and uniformity to the make-up. Pearlescent agents should be understood as referring to iridescent particles which reflect light.

The pigments may be generally present in a proportion of 0 to 20% by weight, relative to the total weight of the composition, and preferably in a proportion of 2 to 15%. They may be white or coloured, inorganic and/or organic, and of usual or nanometric size. Mention may be made, among the inorganic pigments and nanopigments, of titanium dioxide, zirconium dioxide or cerium dioxide, as well as zinc oxide, iron oxide or chromium oxide, nanotitania and ferric blue. Among the organic pigments, mention may be made of carbon black and the lakes commonly used to give the lips and the skin a make-up effect, which are calcium, barium, aluminium or zirconium salts, of acidic dyes such as halo acid, azo or anthraquinone dyes.

When the composition is in the form of an oil-in-water emulsion, the pigments preferably have a hydrophobic surface area or may be treated so as to make their surface hydrophobic; this treatment may be carried out according to the methods known to those skilled in the art; the pigments may be coated, in particular, by silicone compounds such as PDMSs and/or by polymers, in particular polyethylenes. Mention may thus be made of the pigments SA from Maprecos or the pigments PI from Myoshi, since it has been observed that when the pigments were not coated, the product obtained had a non-smooth and/or brittle appearance.

When the composition is in the form of an aqueous gel or solution, it may comprise water-soluble dyes chosen from the usual dyes of the field considered, such as the disodium salt of pumice, the disodium salt of alizarin green, quinoline yellow, the trisodium salt of amaranth, the disodium salt of tartrazine, the monosodium salt of rhodamine, the disodium salt of fuchsin, and xanthophyll.

The pearlescent agents may generally be present in the composition in a proportion of 0 to 20% by weight, preferably to a high level of about 2 to 15% by weight. Among the pearlescent agents which may be envisaged, mention may be made of natural mother-of-pearl, mica coated with titanium oxide, with iron oxide, with natural pigment or with bismuth oxychloride, as well as coloured titanium mica.

The fillers which may be generally present in the composition in a proportion of 0 to 20% by weight, relative to the total weight of the composition, preferably 2 to 10%, may be inorganic or synthetic, lamellar or non-lamellar. Mention may be made of talc, mica, silica, kaolin, nylon powder, polyethylene powder, Teflon, starch, boron nitride, microspheres such as Expancel (Nobel Industrie), polytrap (Dow Corning) and microbeads of silicone resin (Tospearis from Toshiba for example).

The composition may also comprise any additive commonly used in the cosmetic field, such as antioxidants, fragrances, essential oils, preserving agents, cosmetic or pharmaceutical lipophilic or hydrophilic active agents, moisturizers, vitamins, essential fatty acids, sphingolipids, self-tanning compounds such as DHA, and sun screens. A person skilled in the art will take care to select this or these optional additional compound(s), and/or the amount thereof, such that the advantageous properties of the composition according to the invention are not, or are not substantially, adversely affected by the addition envisaged.

These additives may be generally present in the composition in a proportion of 0 to 10% by weight. Depending on their nature, they are present in the aqueous phase or in the fatty phase of the composition.

The compositions according to the invention may be in any form which is suitable for topical application, in particular in the form of a serum, a lotion, a cream, a milk, an aqueous gel, emulsions obtained by dispersion of a fatty phase in an aqueous phase (O/W) or, conversely, (W/O), of liquid or semi-liquid consistency or even pasty or solid.

The emulsions according to the invention thus constitute all or part of a cosmetic, pharmaceutical or hygiene composition.

The compositions according to the invention find an application in particular in the field of making up the skin, semi-mucous membranes, mucous membranes and/or the exoskeleton, and, in this case, are for example in the form of a foundation, a blusher, an eye-shadow, a lipstick, a mascara, an eye-liner or a nail varnish.

They may also be used as a care base for the lips or as a care product for the skin, mucous membranes, semi-mucous membranes and/or the exoskeleton, such as a gel, a cream, a balm or a lotion, or as a hygiene or pharmaceutical product, or alternatively as an antisun or self-tanning product.

They also find an application in the field of haircare, in particular as care creams or gels for the exoskeleton such as the hair, the eyelashes and the eyebrows, or alternatively as an aqueous gel, in particular for styling.

The invention is illustrated in greater detail in the examples which follow.

The examples which follow illustrate the invention without, however, being limiting in nature.

EXAMPLES 1 to 15
Study of the Persistence Properties of Various Emulsions

Various emulsions (foundation) in accordance with the invention were prepared, each emulsion having a different composition.

The emulsions comprise the following compounds:
- a fatty phase
- the copolymer according to the invention (Pemulen TR2 from Goodrich) and optionally:
- a crosslinked poly(2-acrylamido-2-methylpropanesulphonic acid) neutralized with aqueous ammonia, with a viscosity at 25° C. of 16,000 cps, in aqueous 2% solution.
- an optionally crosslinked acrylic acid copolymer (Carbopol 980 from Goodrich)
- polyvinyl alcohol
- surfactants (sorbitan monostearate 20EO; polyglyceryl decaoleate)
- fillers
- PDMS- or polyethylene-coated pigments
- water-soluble dyes
- water qs 100 g The compositions were prepared, in the usual manner, by mixing the ingredients of the fatty phase and the predispersed pigments; the aqueous phase was prepared by mixing the water and the copolymers at 80° C. The two phases were mixed at room temperature with stirring using a turbomixer, and the mixture was left to cool.

Example 1

| | | |
|---|---|---|
| Hydroxylated silicone gum in PDMS (Q2-1403 from Dow Corning) | | 16 g |
| Pemulen TR2 from Goodrich | | 0.1 g |
| Poly(2-acrylamido-2-methylpropanesulphonic acid) | | 0.6 g |
| PDMS-coated pigments | | 10 g |
| Water | qs | 100 g |

The PDMS-coated pigments used in this and other Examples as indicated below were a combination of four pigments. The proportions of pigments used vary, in a manner well-known to those skilled in the art, according to the final color desired. The four pigments used were:
(1) PDMS-coated Iron Oxide (red) pigment marketed under the name "Cosmetic russet SA-C33-8075-10" by Myoshi;
(2) PDMS-coated Iron Oxide (yellow) pigment marketed under the name "Cosmetic yellow SA-C33-8073-10" by Myoshi;
(3) PDMS-coated Iron Oxide (black) pigment marketed under the name "Cosmetic black SA-C33-134-10" by Myoshi; and
(4) PDMS-coated Titanium Oxide (white) pigment marketed under the name "Cosmetic white SA-C47-051-10" by Myoshi.

Example 2

| | | |
|---|---|---|
| Hydroxylated silicone gum in PDMS (Q2-1403 from Dow Corning) | | 16 g |
| Pemulen TR2 from Goodrich | | 0.1 g |
| Poly(2-acrylamido-2-methylpropanesulphonic acid) | | 0.6 g |
| Polyvinyl alcohol | | 0.5 g |
| PDMS-coated pigments | | 10 g |
| Water | qs | 100 g |

Example 3

| | | |
|---|---|---|
| Hydroxylated silicone gum in PDMS (Q2-1403 from Dow Corning) | | 16 g |
| Pemulen TR2 from Goodrich | | 0.1 g |
| Poly(2-acrylamido-2-methylpropanesulphonic acid) | | 0.6 g |
| Polyvinyl alcohol | | 0.5 g |
| Surfactant | | 1.1 g |
| PDMS-coated pigments | | 12 g |
| Water | qs | 100 g |

The surfactant used in this and the following Examples 4, 6, 7, 8, 12, 13, 14, 15, 17, 18, and Comparative 19, Foundation A, was a mixture of 0.1 g sorbitain monostearate (20 OE) and 1 g polyglyceryl decaoleate.

Example 4

| | | |
|---|---|---|
| Hydroxylated silicone gum in PDMS (Q2-1403 from Dow Corning) | | 11 g |
| Cyclopentadimethylsiloxane (volatile cycloD5 silicone) | | 5 g |
| Pemulen TR2 from Goodrich | | 0.1 g |
| Poly(2-acrylamido-2-methylpropanesulphonic acid) | | 0.6 g |
| Polyvinyl alcohol | | 0.5 g |
| Surfactant | | 1.1 g |
| PDMS-coated pigments | | 12 g |
| Water | qs | 100 g |

Example 5

| | | |
|---|---|---|
| Hydroxylated silicone gum in PDMS (Q2-1403 from Dow Corning) | | 8 g |
| Apricot oil | | 8 g |
| Pemulen TR2 from Goodrich | | 0.1 g |
| Carbopol 980 from Goodrich | | 0.6 g |
| Surfactant | | 0.1 g |
| PDMS-coated pigments | | 12 g |
| Water | qs | 100 g |

The surfactant used in this Example and in Example 9 below was sorbitan monostearate 20 OE.

Example 6

| | | |
|---|---|---|
| Hydroxylated silicone gum in PDMS (Q2-1403 from Dow Corning) | | 13 g |
| Cyclopentadimethylsiloxane | | 3 g |
| Pemulen TR2 from Goodrich | | 0.1 g |
| Poly(2-acrylamido-2-methylpropanesulphonic acid) | | 0.5 g |
| Polyvinyl alcohol | | 0.5 g |
| Surfactant | | 1.1 g |
| PDMS-coated pigments | | 14 g |
| Hollow microspheres (Expancel 551 DE20) | | 0.5 g |
| Water | qs | 100 g |

Example 7

| | | |
|---|---|---|
| Hydroxylated silicone gum in PDMS (Q2-1403 from Dow Corning) | | 13 g |
| Cyclopentadimethylsiloxane | | 3 g |
| Pemulen TR2 from Goodrich | | 0.1 g |
| Poly(2-acrylamido-2-methylpropanesulphonic acid) | | 0.5 g |
| Polyvinyl alcohol | | 0.6 g |
| Surfactant | | 1.1 g |
| PDMS-coated pigments | | 14 g |
| Filler (nylon) | | 0.5 g |
| Water | qs | 100 g |

Example 8

| | | |
|---|---|---|
| Hydroxylated silicone gum in PDMS (Q2-1403 from Dow Corning) | | 16 g |
| Pemulen TR2 from Goodrich | | 0.6 g |
| Surfactant | | 1.1 g |
| PDMS-coated pigments | | 12 g |
| Water | qs | 100 g |

Example 9

| | | |
|---|---|---|
| Hydroxylated silicone gum in PDMS (Q2-1403 from Dow Corning) | | 16 g |
| Pemulen TR2 from Goodrich | | 0.1 g |
| Carbopol 980 from Goodrich | | 0.6 g |
| Surfactant | | 0.1 g |
| PDMS-coated pigments | | 10 g |
| Water | qs | 100 g |

Example 10

| | | |
|---|---|---|
| Hydroxylated silicone gum in PDMS (Q2-1403 from Dow Corning) | | 16 g |
| Pemulen TR2 from Goodrich | | 0.1 g |
| Carbopol 980 from Goodrich | | 0.6 g |
| Polyethylene-coated pigments | | 4 g |
| Water | qs | 100 g |

The polyethylene-coated pigments used were a combination of the following four pigments:

(1) polyethylene-coated Iron Oxide (red) pigment marketed under the name "PI-C33-8075-100" by Myoshi;
(2) polyethylene-coated Iron Oxide (yellow) pigment marketed under the name "PI-C33-8073-10" by Myoshi;
(3) polyethylene-coated Iron Oxide (black) pigment marketed under the name "PI-C33-134-10" by Myoshi; and
(4) polyethylene-coated Titanium Oxide (white) pigment marketed under the name "C47-051-PI" by Myoshi.

Example 11

| | | |
|---|---|---|
| Hydroxylated silicone gum in PDMS (Q2-1403 from Dow Corning) | | 16 g |
| Pemulen TR2 from Goodrich | | 0.1 g |
| Carbopol 980 from Goodrich | | 0.6 g |
| Water-soluble dyes | | 0.274 g |
| Water | qs | 100 g |

The water-soluble dyes used were a mixture of 0.11 g quinoline yellow, 0.11 g disodium salt of pumice, and 0.54 g of disodium salt of green alizarin.

Example 12

| | | |
|---|---|---|
| PDMS (10 cSt) | | 10 g |
| Apricot oil | | 10 g |
| Pemulen TR2 from Goodrich | | 0.1 g |
| Poly(2-acrylamido-2-methylpropanesulphonic acid) | | 0.6 g |
| Polyvinyl alcohol | | 0.6 g |
| Surfactant | | 1.1 g |
| PDMS-coated pigments | | 14 g |
| Water | qs | 100 g |

Example 13

| | | |
|---|---|---|
| PDMS (10 cSt) | | 15 g |
| Apricot oil | | 10 g |
| Pemulen TR2 from Goodrich | | 0.1 g |
| Poly(2-acrylamido-2-methylpropanesulphonic acid) | | 0.6 g |
| Polyvinyl alcohol | | 0.6 g |
| Surfactant | | 1.1 g |
| PDMS-coated pigments | | 14 g |
| Water | qs | 100 g |

Example 14

| | | |
|---|---|---|
| PDMS (10 cSt) | | 15 g |
| Pemulen TR2 from Goodrich | | 0.1 g |
| Poly(2-acrylamido-2-methylpropanesulphonic acid) | | 0.6 g |
| Polyvinyl alcohol | | 0.6 g |
| Surfactant | | 1.1 g |
| PDMS-coated pigments | | 14 g |
| Water | qs | 100 g |

Example 15

| | | |
|---|---|---|
| PDMS (10 cSt) | | 6 g |
| Apricot oil | | 10 g |
| Pemulen TR2 from Goodrich | | 0.1 g |
| Poly(2-acrylamido-2-methylpropanesulphonic acid) | | 0.6 g |
| Polyvinyl alcohol | | 0.6 g |
| Surfactant | | 1.1 g |
| PDMS-coated pigments | | 14 g |
| Water | qs | 100 g |

Foundations are thus obtained which spread easily on the skin without giving a greasy feel and do not transfer on contact with a fabric.

These foundations give a certain sensation of freshness when they are applied to the skin.

The persistence properties of these emulsions were then determined.

For this, 0.05 g of each emulsion was applied to an area of 50 cm$^2$ on the forearm and the composition applied was then left to dry for 5 minutes. A strip of polyester fabric was then applied over the part of the forearm treated. Using a machine, the strip was placed in a vertical translational motion, in contact with the forearm treated. The fabric was kept taut by means of a counterweight, thus creating rubbing of the fabric during the translation. 10 back-and-forth rubbing motions were carried out.

The coloured traces possibly deposited on the fabric were then graded according to the following grading:

highly stained fabric: grade=0 stain-free fabric: grade=10

A foundation is considered to transfer little when the grade is equal to or greater than 8.5.

The results obtained are reported in the table below.

| Example | Grade |
|---|---|
| Example 1 | 9 |
| Example 2 | 9.5 |
| Example 3 | 9 |
| Example 4 | 9.5 |
| Example 5 | 10 |
| Example 6 | 9 |
| Example 7 | 9.5 |
| Example 8 | 9.5 |
| Example 9 | 10 |
| Example 10 | 8.5 |
| Example 11 | 9.5 |
| Example 12 | 8.5 |
| Example 13 | 9 |
| Example 14 | 8.5 |
| Example 15 | 8.5 |

It emerges from these results that the emulsions according to the invention have good persistence properties and do not transfer onto the fabric.

This is also the case when oils of plant origin (apricot oil) are present in the composition, at a content which may be up to 10% by weight.

Examples 1 and 2, which are readily comparable, show also that the association Pemulen TR2-Polyvinyl alcohol is particularly outstanding in order to limit the transfer of a composition according to the invention.

Example 16

Comparative Example

The following composition was prepared for comparison:

Example 16

| | | |
|---|---|---|
| Hydroxylated silicone gum in PDMS (Q2-1403 from Dow Corning) | | 16 g |
| Carbopol 980 from Goodrich | | 0.7 g |
| PDMS-coated pigments | | 12 g |
| Water | qs | 100 g |

It was observed that it was not possible to disperse the fatty substances since there was not enough Carbopol.

EXAMPLES 17 and 18

These examples aim at showing that the presence of a large amount of hydrocarbon oil (plant oil in the present case) is unfavorable in regards to avoiding transfer. These examples can be compared to the preceding examples 3 and 4.

Example 17

| | | |
|---|---|---|
| Hydroxylated silicone gum in PDMS (Q2-1403 from Dow Corning) | | 13 g |
| Apricot oil | | 12 g |
| Pemulen TR2 from Goodrich | | 0.1 g |
| Poly(2-acrylamido-2-methylpropane sulphonic acid) | | 0.6 g |
| Polyvinyl alcohol | | 0.6 g |
| Surfactant | | 1.1 g |
| PDMS-coated pigments | | 14 g |
| Water | qs | 100 g |

Example 18

| | | |
|---|---|---|
| Hydroxylated silicone gum in PDMS (Q2-1403 from Dow Corning) | | 13 g |
| Isostearyl neopentanoate | | 12 g |
| Pemulen TR2 from Goodrich | | 0.1 g |
| Poly(2-acrylamido-2-methylpropane-sulphonic acid) | | 0.6 g |
| Polyvinyl alcohol | | 0.6 g |
| Surfactant | | 1.1 g |
| PDMS-coated pigments | | 14 g |
| Water | qs | 100 g |

For these examples 17 and 18, the persistence properties of the emulsions were determined according to the test described above. The following results are obtained.

| Example | Grade |
|---|---|
| Example 17 | 6 |
| Example 18 | 6.5 |

Example 19

Comparative Example

This example aims at showing the improvement provided, in regards to the limitation of the transfer of a composition, by the use of Pemulen TR2; one has thus realized a foundation A according to the invention and comprising Pemulen TR2 and a foundation B, having the same composition as A but in which the Pemulen TR2 has been replaced by a classical surfactant system stearic acid/stearate - triethanolamine. The compositions are given hereinafter:

| Foundation A: | | |
|---|---|---|
| PDMS (10 cSt) | | 10 g |
| Apricot oil | | 10 g |
| Pemulen TR2 from Goodrich | | 0.1 g |
| Poly(2-acrylamido-2-methylpropane-sulphonic acid) | | 0.6 g |
| Polyvinyl alcohol | | 0.6 g |
| Surfactant | | 1.1 g |
| PDMS-coated pigments | | 14 g |
| Water | qs | 100 g |

| Foundation B: | | |
|---|---|---|
| PDMS (10 cSt) | | 10 g |
| Apricot oil | | 10 g |
| Stearic acid/stearate | | 4.4 g |
| Poly(2-acrylamido-2-methylpropane-sulphonic acid) | | 0.6 g |
| Polyvinyl alcohol | | 0.6 g |
| Triethanolamine | | 1.1 g |
| PDMS-coated pigments | | 14 g |
| Water | qs | 100 g |

These foundations have been prepared in the usual manner, by mixing the ingredients of the fatty phase and the predispersed pigments; the aqueous phase was then prepared and the two phases were mixed at 65° C. under stirring using a turbomixer. The mixture was then left to cool.

The persistence properties of these emulsions were then determined in the same manner as in examples 1 to 15. The results obtained are reported in the table below:

| Foundation | Grade |
|---|---|
| A (invention) | 9 |
| B (comparative) | 6 |

We claim:

1. A process for improving the transfer resistance of a composition comprising an aqueous phase, said process comprising introducing into the composition an amount effective for the purpose of improving the transfer resistance of the composition, of at least one optionally crosslinked copolymer, said copolymer comprising a first fraction derived from at least one first monomer chosen from a monoolefinically unsaturated $C_3$–$C_6$ carboxylic acid monomer and an anhydride thereof, said first fraction being present in the copolymer in an amount greater than about 50 wt %, and a second fraction derived from at least one second monomer chosen from a fatty-chain monomeric ester of an acrylic acid.

2. A process comprising the step of forming a film of a composition comprising an aqueous phase, said film having at least one property chosen from non-transfer, non-migration, and improved transfer resistance, wherein said composition comprises an effective amount of at least one optionally crosslinked copolymer, said copolymer comprising a first fraction derived from at least one first monomer chosen from a monoolefinically unsaturated $C_3$–$C_6$ carboxylic acid monomer and an anhydride thereof, said first fraction being present in an amount greater than about 50 wt %, and a second fraction derived from at least one second monomer chosen from a fatty-chain monomeric ester of acrylic acid to impart said at least one property.

3. A process, said process comprising introducing into a composition comprising an aqueous phase, for the purpose of limiting, decreasing, preventing, or eliminating the transfer thereof, an effective amount of at least one optionally crosslinked copolymer, said copolymer comprising a first fraction derived from at least one first monomer chosen from a monoolefinically unsaturated $C_3$–$C_6$ carboxylic acid monomer and an anhydride thereof, said first fraction being present in the copolymer in an amount greater than about 50 wt %, and a second fraction derived from at least one second monomer chosen from a fatty-chain monomeric ester of an acrylic acid.

4. A process according to claim 3, wherein said amount effective of said copolymer ranges from 0.01 to 3% by weight relative to the total weight of the composition.

5. A process according to claim 4 wherein said amount effective of said copolymer ranges from 0.02 to 0.6% by weight relative to the total weight of the composition.

6. A process according to claim 5 wherein said amount effective of said copolymer ranges from 0.05 to 0.2% by weight relative to the total weight of the composition.

7. A process according to claim 3 wherein said composition further comprises at least one additional ingredient selected from:

crosslinked and at least 90% neutralized poly(2-acrylamido-2-methylpropanesulphonic acid) polymers and optionally crosslinked acrylic acid homo- and copolymers, and salts thereof.

8. A process according to claim 3 wherein said composition further comprises polyvinyl alcohol.

9. A process according to claim 3 wherein said composition is in the form of an oil-in-water emulsion, a water-in-oil emulsion, a multiple emulsion, an aqueous gel or an aqueous, aqueous-alcoholic or multi-phase solution.

10. A process according to claim 9 wherein said multi-phase solution is a water/powder solution or a water/oil/powders solution.

11. A process according to claim 3 wherein said composition comprises a fatty phase which comprises a maximum of about 10% by weight of non-volatile hydrocarbon oil.

12. A process according to claim 11 wherein said fatty phase comprises less than 8% by weight of non-volatile hydrocarbon oil.

13. A process according to claim 12 wherein said fatty phase comprises less than 5% by weight of non-volatile hydrocarbon oil.

14. A process according to claim 13 wherein said fatty phase comprises no non-volatile hydrocarbon oil.

15. A process according to claim 11, wherein said composition comprises a fatty phase which comprises only at least one silicone fatty substance.

16. A process according to claim 15 wherein said at least one silicone fatty substance is selected from:

volatile cyclic oils optionally mixed with PDMSs and/or phenyl silicone oils, and silicone gums mixed with optionally volatile silicone oils.

17. A process according to claim 16 wherein said silicone gums are selected from phenylated and hydroxylated silicone gums.

18. A process according to claim 3 wherein the composition is in the form of a composition for making up the skin, semi-mucous membranes, mucous membranes and/or the exoskeleton.

19. A process according to claim 18 wherein said composition is in the form of a foundation, a blusher, an eye-shadow, a lipstick, a mascara, an eye-finer, a nail varnish, a care base for the lips, a care product for the skin, mucous membranes, semi-mucous membranes and/or the exoskeleton, a hygiene or pharmaceutical product, an anti-sun or self-tanning product, or a haircare product.

20. A process according to claim 3 wherein said cosmetic, dermatological, hygiene and/or pharmaceutical composition is a composition to make up and/or care for the skin, mucous membranes, semi-mucous membranes and/or the exoskeleton.

* * * * *

UNITED STATES PATENT AND TRADEMARK OFFICE
CERTIFICATE OF CORRECTION

PATENT NO. : 6,395,262 B1
DATED : May 28, 2002
INVENTOR(S) : Sohpie Favre et al.

It is certified that error appears in the above-identified patent and that said Letters Patent is hereby corrected as shown below:

<u>Title page,</u>
Item [75], inventors, "Sophie Favre; Nadia Terren, both of Chevilly-Larue;" should read -- Sophie Favre, Chevilly-Larue; Nadia Terren, Bourg La Reine; --.

<u>Column 19,</u>
Line 3, "eye-finer" should read -- eye-liner --.

Signed and Sealed this

Tenth Day of December, 2002

JAMES E. ROGAN
*Director of the United States Patent and Trademark Office*